US007699057B2

(12) United States Patent
Miller et al.

(10) Patent No.: US 7,699,057 B2
(45) Date of Patent: Apr. 20, 2010

(54) METHODS FOR TREATING SKIN LESIONS

(75) Inventors: Richard L. Miller, Maplewood, MN (US); James H. Lee, St. Paul, MN (US); Terrance L. Fox, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1735 days.

(21) Appl. No.: 10/799,997

(22) Filed: Mar. 12, 2004

(65) Prior Publication Data
US 2004/0181130 A1   Sep. 16, 2004

Related U.S. Application Data

(60) Provisional application No. 60/454,244, filed on Mar. 13, 2003.

(51) Int. Cl.
A61B 19/00   (2006.01)

(52) U.S. Cl. .................................................. 128/898

(58) Field of Classification Search ................ 128/898; 600/306; 606/39
See application file for complete search history.

(56) References Cited

U.S. PATENT DOCUMENTS

| 3,314,941 | A | 4/1967 | Littell et al. |
| 4,689,338 | A | 8/1987 | Gerster |
| 4,698,348 | A | 10/1987 | Gerster |
| 4,929,624 | A | 5/1990 | Gerster et al. |
| 4,988,815 | A | 1/1991 | Andre et al. |
| 5,037,986 | A | 8/1991 | Gerster |
| 5,175,296 | A | 12/1992 | Gerster |
| 5,238,944 | A | 8/1993 | Wick et al. |
| 5,266,575 | A | 11/1993 | Gerster |
| 5,268,376 | A | 12/1993 | Gester |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,446,153 | A | 8/1995 | Lindstrom et al. |
| 5,482,936 | A | 1/1996 | Lindstrom |
| 5,693,811 | A | 12/1997 | Lindstrom |
| 5,741,908 | A | 4/1998 | Gerster et al. |
| 5,756,747 | A | 5/1998 | Gerster et al. |
| 5,939,090 | A | 8/1999 | Beaurline et al. |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A | 8/2000 | Gerster et al. |
| 6,194,425 | B1 | 2/2001 | Gerster et al. |
| 6,245,776 | B1 | 6/2001 | Skwierczynski et al. |
| 6,331,539 | B1 | 12/2001 | Crooks et al. |
| 6,376,669 | B1 | 4/2002 | Rice et al. |
| 6,451,810 | B1 | 9/2002 | Coleman et al. |
| 6,518,265 | B1 | 2/2003 | Kato et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |
| 6,545,017 | B1 | 4/2003 | Dellaria et al. |
| 6,558,951 | B1 | 5/2003 | Tomai et al. |
| 6,573,273 | B1 | 6/2003 | Crooks et al. |
| 6,656,938 | B2 | 12/2003 | Crooks et al. |
| 6,660,735 | B2 | 12/2003 | Crooks et al. |
| 6,660,747 | B2 | 12/2003 | Crooks et al. |
| 6,664,260 | B2 | 12/2003 | Charles et al. |
| 6,664,264 | B2 | 12/2003 | Dellaria et al. |
| 6,664,265 | B2 | 12/2003 | Crooks et al. |
| 6,667,312 | B2 | 12/2003 | Bonk et al. |
| 6,670,372 | B2 | 12/2003 | Charles et al. |
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 6,890,904 | B1 * | 5/2005 | Wallner et al. ................. 514/14 |
| 7,521,459 | B2 | 4/2009 | Baumann et al. |
| 2002/0016332 | A1 | 2/2002 | Slade |
| 2002/0055517 | A1 | 5/2002 | Smith |
| 2002/0058674 | A1 | 5/2002 | Hedenstrom et al. |
| 2002/0110840 | A1 | 8/2002 | Tomai et al. |

(Continued)

FOREIGN PATENT DOCUMENTS

EP   0 394 026   10/1990

(Continued)

OTHER PUBLICATIONS

Wozniak, et al, "The Amination of 3-nitro-1, 5-naphthyridines by Liquid Ammonia/Potassium Permanganate[1,2]. A New and Convenient Amination Method.", *Journal of the Royal Netherlands Chemical Study*, 102, pp. 511-513, Dec. 12, 1983.

Brennan, et al, "Automated Bioassay of Interferons in Micro-test Plates", *Biotechniques*, Jun./Jul., 78, 1983.

Testerman, et al., "Cytokine Induction by the Immunomodulators Imiquimod and S-27609", *Journal of Leukocyte Biology*, vol. 58, pp. 365-372, Sep. 1995.

Bachman, et al, "Synthesis of Substituted Quinolylamines. Derivatives of 4-Amino-7-Chloroquinoline", *J. Org. Chem*, 15, pp. 1278-1284 (1950).

Jain, et al, "Chemical and Pharmacological Investigations of Some ω-Substituted Alkylamino-3-aminopyridines", *J. Med. Chem.*, 11, pp. 87-92 (1968).

Baranov, et al., *Chem. Abs.* 85, 94362, (1976).

(Continued)

*Primary Examiner*—William H. Matthews

(57) ABSTRACT

Methods for diagnosing skin lesions are disclosed. Generally, the method include topically administering an IRM compound to a treatment area for a period of time and in an amount effective to cause a visible change in the appearance of a skin lesion including, in some cases, causing subclinical lesions to become visible. Suitable IRM compounds include agonists of one or more TLRs.

3 Claims, No Drawings

U.S. PATENT DOCUMENTS

| | | | |
|---|---|---|---|
| 2003/0022302 | A1 | 1/2003 | Lewis et al. |
| 2003/0130299 | A1 | 7/2003 | Crooks et al. |
| 2003/0133913 | A1 | 7/2003 | Tomai et al. |
| 2003/0139364 | A1 | 7/2003 | Krieg et al. |
| 2003/0161797 | A1 | 8/2003 | Miller et al. |
| 2003/0199538 | A1 | 10/2003 | Skwierczynski et al. |
| 2003/0232852 | A1 | 12/2003 | Lindstrom et al. |
| 2004/0010007 | A1 | 1/2004 | Dellaria et al. |
| 2004/0014779 | A1 | 1/2004 | Gorden et al. |
| 2004/0023870 | A1 | 2/2004 | Dedera et al. |

FOREIGN PATENT DOCUMENTS

| | | |
|---|---|---|
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 02/36592 | 5/2002 |
| WO | WO 03/089602 | 10/2003 |
| WO | WO 03/103584 | 12/2003 |

OTHER PUBLICATIONS

Berényi, et al, "Ring Transformation of Condensed Dihydro-astriazines", *J. Heterocyclic Chem.*, 18, pp. 1537-1540 (1981).

Chollet, et al, "Development of a Topically Active Imiquimod Formulation", *Pharmaceutical Development and Technology*, 4(1), pp. 35-43 (1999).

Izumi, et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines", *Bioorganic & Medicinal Chemistry*, 11, pp. 2541-2550 (2003).

Hornung et al., "Quantitative Expression of Toll-Like Receptor 1-10 mRNA in Cellular Subsets of Human Peripheral Blood Mononuclear Cells and Sensitivity to CpG Oligodeoxynucleotides[1]", *The Journal of Immunology*, 2002, 168; pp. 4531-4537.

Hemmi et al., "Small anti-viral compounds activate immune cells via the TLR7 MyD88-dependent Signaling pathway", *Nature Immunology*, vol. 3, No. 2; Feb. 2002; pp. 196-200.

Medzhitov, "Toll-Like Receptors and Innate Immunity", *Nature Reviews Immunology*, vol. 1; Nov. 2001, pp. 135-145.

Jurk et al. "Human TLR7 and TLR8 independently confer responsiveness to the antiviral compound R-848", *Nature Immunology*, Jun. 2002, vol. 3, No. 6; p. 1.

Akira et al., "Toll-like receptors: critical proteins linking innate and acquired immunity", *Nature Immunology*, Aug. 2001, vol. 2, No. 8; pp. 675-680.

Heil et al.; "Synthetic immunostimulatory compounds activate immune cells via TLR7 and TLR8"; 33th Annual Meeting of the Deutsche Gessellschaft für lmmunologie, Marburg 2002—Abstract C.6.

Akira S. et al., "Recognition of pathogen-associated molecular patterns by TLR family", *Immunology Letters*, 2003, vol. 85, pp. 85-95.

Ozinsky A. et al., "The repertoire for pattern recognition of pathogens by the innate immune system is defined by cooperation between Toll-like receptors", *Proc. Nat. Acad. Sci.*, Dec. 2000, vol. 97, No. 25, pp. 13766-13771.

Gorden et al., "Synthetic TLR Agonists Reveal Functional Differences between Human TLR7 and TLR8", *The Journal of Immunology*, 2005, vol. 174, pp. 1259-1268.

Sauder et al., "Randomized, Single-Blind, Placebo-Controlled Study of Topical Application of the Immune Response Modulator Resiquimod in Healthy Adults", *Antimicrobial Agents and Chemotherapy*, Dec. 2003, vol. 47, No. 12, pp. 3846-3852.

\* cited by examiner

METHODS FOR TREATING SKIN LESIONS

CROSS-REFERENCE TO RELATED APPLICATION

This application claims priority to U.S. Provisional Patent Application No. 60/454,244, filed Mar. 13, 2003.

BACKGROUND OF THE INVENTION

Nonmelanoma skin cancer is the most common cancer in the United States, with an estimated annual incidence of more than 1,000,000 cases. Basal cell carcinomas (BCC) account for 70 to 80% of nonmelanoma skin cancers. Squamous cell carcinoma (SCC), while representing only about 20% of nonmelanoma skin cancers, are significant because of their ability to metastasize and accounts for over 2300 deaths annually. The incidence of nonmelanoma skin cancer continues to increase. Early diagnosis can be lifesaving and it is important that physicians know what treatment modalities will be the most effective.

Nonmelanoma skin cancers may be treated using various procedures that excise or kill the cancerous cells. Removal of the entire tumor is essential to prevent tumor recurrence and, in some cases, metastasis. However, the clinically visible portion of a lesion may represent only a fraction of the total lesion, making excision of the entire lesion difficult. Currently, even with a precise preoperative diagnosis, complete excision of nonmelanoma skin cancer is not always achieved. Incomplete excision of these carcinomas requires further treatment such as, for example, a second excision procedure to remove the residual tumor. Thus, improved methods of diagnosis that identify the complete margins of such lesions are needed.

SUMMARY OF THE INVENTION

It has been found that certain small molecule immune response modifier (IRM) compounds can be used for diagnosing and treating skin lesions.

Accordingly, the present invention provides a method of diagnosing a skin lesion. Generally, the method includes administering to a treatment area of the skin an IRM compound for a period of time and in an amount sufficient to permit visualization of a skin lesion in the treatment area.

In another aspect, the present invention provides a method of visualizing the margins of a skin lesion. Generally, the method includes administering to a treatment area of the skin an IRM compound for a period of time and in an amount sufficient to permit visualization of the margins of a skin lesion in the treatment area.

In another aspect, the present invention provides a method of visibly accentuating the margins of a skin lesion. Generally, the method includes administering to a treatment area that includes a clinically visible skin lesion an IRM compound for a period of time and in an amount sufficient to visibly accentuate the margins of the skin lesion.

In another aspect, the present invention provides a method of pretreating a skin lesion prior to an ablation procedure. Generally, the method includes administering to a treatment area that includes a skin lesion an IRM compound for a period of time and in an amount sufficient to visibly accentuate the margins of the skin lesion.

In another aspect, the present invention provides methods of visualizing a subclinical skin lesion. Generally, the method includes administering to a treatment area an IRM compound for a period of time and in an amount sufficient to cause a subclinical skin lesion in the treatment area to become apparent, and then visualizing the skin lesion.

In another aspect, the present invention provides a method of treating a skin lesion. Generally, the method includes administering to a treatment area that includes at least one skin lesion an IRM compound for a period of time and in an amount sufficient to permit visualization of the margins of the skin lesion, and then subjecting the skin lesion to an ablation procedure.

In some embodiments of the invention, the various methods may further include subjecting the skin lesion to an ablation procedure such as, for example, Mohs micrographic surgery, surgical excision, cryotherapy, or radiotherapy.

In some embodiments of the invention, the skin lesion may be a neoplastic skin lesion, a subclinical lesion, a nonmelanoma skin cancer, or a premalignant skin lesion. In some embodiments, the skin lesion may be a basal cell carcinoma, a squamous cell carcinoma, lentigo maligna, Bowen's disease, or actinic keratoses.

In some embodiments of the invention, the IRM may be an agonist of at least one TLR; including an agonist of TLR4, TLR7, TLR8 or both TLR7 and TLR8.

Various other features and advantages of the present invention should become readily apparent with reference to the following detailed description, examples, and claims. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

The present invention provides methods for diagnosing skin lesions, accentuating the margins of skin lesions, visualizing subclinical skin lesions, and treating skin lesions. Generally, the methods include administering an IRM compound to a treatment area that includes a skin lesion. Administering an IRM compound to a lesion, whether or not the lesion is clinically visible when the IRM compound is administered, can induce a subject's immune system to respond to immunologic stimuli of the lesion, thereby initiating or enhancing a localized immune response against the lesion. This localized immune response can lead to visible changes in the appearance of the lesion (including, if the lesion is subclinical, making the lesion apparent). Such visible changes may result from, for example, inflammation and/or infiltration of immune cells into the lesion, and may include one or more of, for example, erosion, erythema (redness), and edema (swelling).

Unaffected tissues surrounding the lesion are not targeted by the immune response that is induced by administering the IRM compound. As a result, the unaffected tissues surrounding the lesion do not manifest the visible changes observed in the lesion (e.g., erosion, redness, and/or increased swelling) when the IRM compound is administered. Thus, the erosion, increased swelling and/or redness of the lesion can be used to visually distinguish the tissue of the lesion from the surrounding unaffected tissue. The visible change in the appearance of the lesion can accentuate the margins of the lesion, allowing one to more accurately determine the margins of a lesion.

Administering an IRM compound can induce visible changes in the appearance of lesions that already are clinically visible. Administering an IRM compound also can induce changes in subclinical lesions that render the subclinical lesions visible and, therefore, can assist in the detection and diagnosis of subclinical lesions.

As used herein, "clinically visible" lesions are lesions that are visible, apparent, or otherwise detected without administering an IRM compound. As used herein, "subclinical" lesions are lesions that are present, but because of their location or small size are not visible, apparent, or otherwise detected—i.e., lesions that are not clinically visible. For clarity and consistency, subclinical lesions that become visible as a result of administering and IRM compound may still be referred to as subclinical lesions even though, after administering an IRM compound, the lesions have become visible, apparent, or otherwise detected.

As used herein, "margin" and variations thereof refer to the tissue surrounding a tumor or lesion. More particularly, as used herein, "margins" refers to the edges, borders, or boundaries of a lesion. The margin is the region surrounding a lesion in which the normal, healthy tissue may have been altered by the presence of the lesion. For example, a tumor margin can include tumor cells that have grown beyond the visibly discernable edge of the tumor and can also include stromal regions that have been altered due to the presence of the tumor. In the case of ablation of a lesion, the margin includes tissues that usually appear to be normal to the naked eye that are removed along with the discernible lesion. The margin can generally extend from about 0.2 cm to about 3 cm from a primary lesion, but can be greater depending upon the size of the primary lesion.

As used herein, a "treatment area" is an area of the skin to which an IRM compound is administered. In some cases, a treatment area may be defined by the presence of one or more clinically visible lesions. In such cases, the treatment area may include the clinically visible lesions, including the margins, as well as tissue located between clinically visible lesions. In other cases, a treatment area may be any area to which an IRM compound is administered that lacks clinically visible lesions. For example, a treatment area may be selected because the area is at risk for developing certain types of skin lesions—e.g., areas of the face, scalp, neck, and hands may be at particular risk for developing actinic keratoses, basal cell carcinoma, melanoma, etc. IRM compound may be administered to such areas periodically as a treatment to make diagnosis of such lesions more sensitive.

Lesions that may be diagnosed by the methods of the present invention include lesions of the skin, mucosal surfaces, tissues, and organs. Lesions may be of any known histological form such as, for example, tumors, macules, papules, nodules, plaques, vesicles, bullas, blisters, wheals, scale, erosions, and ulcers. Skin lesions include, but are not limited to, premalignant skin lesions, malignant skin lesions, neoplastic skin lesions, nonmelanoma skin cancers, premalignant epidermal lesions, malignant epidermal lesions, epidermal lesions, dermal lesions, and superficial skin cancers. Skin lesions also include non-neoplastic lesions, including subcutaneous lesions and cutaneous lesions. Such non-neoplastic lesions can include, for example, warts (caused, for example by the human papilloma virus (HPV)), epidermodysplasia verruciformis, molluscum contagiosum, the lesions of leishmaniasis, and keloids. Nonmelanoma skin lesions to be diagnosed by the methods of the present invention include, but are not limited to, basal cell carcinomas, squamous cell carcinomas, actinic keratosis, and in situ squamous cell carcinomas (also called Bowen's disease).

Lesions that may be diagnosed by the methods of the present invention include basal cell carcinoma (BCC). BCC, a subtype of nonmelanoma skin cancer, is a malignancy arising from epidermal basal cells. BCC is a potentially fatal disease linked to sun exposure. The natural history of BCC is that of a slowly enlarging, locally invasive neoplasm. The degree of destruction and risk of recurrence vary with the size, duration and location of the tumor; the histologic subtype; the presence of recurrent disease; and various patient characteristics. Lesions located on the central face (e.g., the nose, the nasolabial fold, or the periorbital or perioral area), the ears, or the scalp are associated with a higher risk. Small nodular, pigmented, cystic, or superficial BCC respond well to treatments. Large nodular, micronodular, noduloulcerative, adenoid, infiltrative, and especially morpheaform BCCs tend to be more aggressive. Mortality rates due to BCC are low, but its increasing incidence and prolonged morbidity means the disease is costly to treat. Advanced lesions may ulcerate and extensive local invasion of bone or facial sinuses may occur. Early recognition and effective treatment are therefore important.

The current treatments for BCC include electrodessication and curettage (ED&C), surgical excision, Mohs micrographic surgery (MMS), cryosurgery, radiation therapy, and treatment with 5-fluorouracil. Newer treatment modalities include photodynamic therapy and the topical application of a 5% imiquimod cream, which effectively resolves BCC lesions. The mode of therapy chosen depends on tumor characteristics, age, medical status, preferences of the patient, and other factors. ED&C is the method commonly employed for low-risk tumors (e.g., a small primary tumor of a less aggressive subtype in a favorable location). Surgical excision, which offers the advantage of histologic control, is often selected for more aggressive tumors or those in high-risk locations, or, in many instances, for esthetic reasons. Cryosurgery using liquid nitrogen may be used in certain low-risk tumors. Radiation therapy, while not employed as often as surgical modalities, offers an excellent chance for cure in many cases of BCC. It is useful in patients not considered surgical candidates and as a surgical adjunct in high-risk tumors. MMS is a specialized type of surgical excision that permits the ultimate in histologic control and preservation of uninvolved tissue. It is preferred for recurrent lesions or lesions that are in a high-risk location or are large and ill defined, and where maximal tissue conservation is critical (e.g., the eyelids). Topical chemotherapy with agents such as 5-fluorouracil (5FU) cream has limited usefulness in the management of BCC, being used for treating superficial BCC. Photodynamic therapy, which employs selective activation of a photoactive drug by visible light, may be useful in patients with numerous tumors. Lasers can also be used for the treatment of skin cancer. For reviews of BCC treatment modalities see, for example, Stockfleth and Sterry (*Recent Results Cancer Res* (2002) 160:259-68) and Kuijpers et al. (*Am J Clin Dermatol* 2002;3(4):247-59).

Lesions that may be diagnosed by the methods of the present invention also include squamous cell carcinoma (SCC). SCC, a subtype of nonmelanoma skin cancer, is the most common tumor arising in sun-exposed skin in older people. Implicated as predisposing factors, in addition to sunlight, are industrial carcinogens (tars and oils), chronic ulcers, old burn scars, ingestion of arsenicals, ionizing radiation, and (in the oral cavity) tobacco and betel nut chewing. Primary cutaneous SCC is a malignant neoplasm of keratinizing epidermal cells. Unlike BCC, which has very low metastatic potential, SCC can metastasize and grow rapidly. The clinical features of SCC can vary widely. Commonly, SCC first appears as an ulcerated nodule or a superficial erosion on the skin or lower lip. The margins of the tumor may be ill defined, and fixation to underlying structures may occur. Surgical excision, MMS, and radiation are standard methods of treatment of SCC. Cryosurgery and ED&C can be used, particularly for the treatment of small primary tumors. Metastases can be treated with lymph node dissection, irradiation, or both. Systemic chemotherapy combinations that include cisplatin may also be used for the treatment of metastatic SCC.

Before the development of overt malignancy of the epidermis, a series of progressively dysplastic changes occur. SCC has several premalignant forms (e.g., actinic keratosis, actinic cheilitis, and some cutaneous horns), and in situ forms (e.g., Bowen's disease) that are confined to the epidermis.

Lesions that may be diagnosed by the methods of the present invention also include actinic keratosis (AK). Actinic keratoses are hyperkeratotic papules and plaques that occur on sun-exposed areas. Exposure to ionizing radiation, hydrocarbons, and arsenicals may induce similar lesions. Skin sites commonly affected can include the face, arms, scalp, and dorsum of the hands. Similar lesions may develop on the lips and are called actinic cheilitis. While the potential for malignant degeneration is low in individual lesions, the risk of SCC increases with larger numbers of AK lesions. AK lesions become malignant frequently enough to warrant local eradication of these potential precursor lesions. This is usually accomplished by curettage, cryotherapy, or topical application of chemotherapeutic agents.

Lesions that may be diagnosed by the methods of the present invention also include the lesions of Bowen's disease. Bowen's disease is a precancerous lesion, which presents as a scaling, erythematous plaque. It may develop into invasive SCC in up to 20% of cases. Thus treatment of the in situ lesions of Bowen's disease reduces the subsequent risk of invasive disease. It is often treated by surgical excision and direct closure. Alternative treatments may include cryotherapy, curettage and cautery, radiation, ultrasonic surgical aspiration (Otani et al., *Plast Reconstr Surg* (2001) 108(1): 68-72), and photodynamic therapy (Wong et al., *Dermatol Surg* (2001) 27(5):452-6).

Lesions that may be diagnosed by the methods of the present invention also include the lesions of lentigo maligna. Lentigo maligna is a preinvasive form of melanoma induced by long-term cumulative ultraviolet injury. Lentigo maligna typically refers to lesions that are confined to the epidermis, whereas lentigo maligna melanoma typically refers to lesions that violate the dermis, thereby establishing metastatic potential. The most frequent findings suggesting early melanoma are changes in size or color of a new, pigmented lesion or an existing mole. Lentigo maligna most commonly affects the sun-exposed skin of the head and neck, with a predilection for the nose and cheek. Less common sites include the arm, leg, and trunk. The conjunctivae and oral mucosa may become involved when a cutaneous lentigo maligna spreads onto mucosal surfaces. Radiotherapy, cryotherapy, chemotherapy, and/or surgical may be used to treat lentigo maligna. Because the actual margins of the lesion usually extend beyond the clinically apparent margin, removal of the entire lesion may be difficult.

Ablation methods suitable for practicing certain embodiments of the invention include all methods used to physically remove a skin lesion from its location in situ. Current clinical treatments for the ablation of skin lesions include, but are not limited to, electrodessication and curettage (ED&C), cryosurgery, radiation therapy, photodynamic therapy, and excision procedures such as, for example, surgical excision and Mohs micrographic surgery (MMS). MMS is an exacting surgical technique for the removal of a nonmelanoma skin cancer. The technique requires the sequential removal of involved tissue in thin layers. Each layer undergoes a histological examination in which the layer is sectioned on a microtome and examined microscopically. From the histological examination of the sequential layers a tissue map is prepared to delineate areas of residual tumor as well as normal, uninvolved tissue. Subsequent tissue layers are removed as dictated by microscopic examination and the process is repeated until the entire tumor has been resected. Due to this microscopic control, cure rates are extremely high for basal and squamous cell cancers.

With all methods of ablation, removal of the entire lesion is essential to limit and prevent tumor recurrence and, in some cases, metastasis. However, this can be difficult to achieve. Even with a precise preoperative diagnosis, complete excision of nonmelanoma skin cancers is not always achieved (Hallock and Lutz, *Plast Reconstr Surg* (2001) 107(4):942-7). For example, rates of incomplete excision of BCC can vary from 5% to 25% among medical centers worldwide (Die and Macleod, *ANZ J. Surg.* (2002) 72(3):219-21). One difficulty is that the margins of the lesion can be difficult to visualize. Another difficulty can be that the clinically visible portion of the lesion may represent only a small fraction of the total lesion. Lesions may have clinically invisible outgrowths or satellites. Also, complete excision of a lesion can be more difficult at some anatomical sites. The frequency of incomplete excision of BCC is higher for lesions located on the eyebrow, the postauricular area, the nose, and the temple (Kumar et al., *Br J Plast Surg* (2002) 55(8):616-22). Because of the risks of recurrence and metastases, incomplete excision leads to further surgery or prolonged follow-up, thus significantly affecting patient outcomes.

In one illustrative embodiment of the invention, an IRM compound administered to treat subjects having clinically visible AK lesions experienced an increase in the number of AK lesions during the treatment period (see Table 1, Examples). Thus, a surprising additional benefit of treating clinically visible AK lesions with the IRM compound was that the treatment effectively uncovered subclinical lesions. Subjects who experienced complete resolution of baseline AK lesions also experienced increased AK lesion counts during the treatment period at a greater rate than those who did not experience complete resolution of their baseline AK lesions. Thus, the increase in AK lesion counts observed in those treated with IRM appears to be due to the appearance of subclinical lesions rather than the formation of new lesions.

In certain embodiments, the present invention provides a method for treating skin lesions. First, an IRM compound is administered to a treatment area that includes a skin lesion for a period of time and in an amount sufficient to permit visualization of the margins of the skin lesion. Then, the skin lesion is subjected to an ablation procedure such as, for example, Mohs micrographic surgery, surgical excision, cryotherapy, or radiotherapy. The improved visualization of the margins of the skin lesions allows for the more complete ablation of the skin lesion.

IRM compounds useful in the methods of the invention include compounds that possess potent immunomodulating activity such as, for example, antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 4,988,815;

5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,541,485; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; European Patent 0 394 026; U.S. Patent Publication Nos. 2002/0016332; 2002/0055517; 2002/0110840; 2003/0133913; 2003/0199538; and 2004/0014779; and International Patent Publication Nos. WO 01/74343; WO 02/46749 WO 02/102377; WO 03/020889; WO 03/043572; WO 03/045391; and WO 03/103584.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08595), and certain 3-β-D-ribofuranosylthiazolo[4,5-d]pyrimidine derivatives derivatives (such as those described in U.S. Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO 00/75304.

Other IRMs include biological molecules such as aminoalkyl glucosaminide phosphates (AGPs) and are described, for example, in U.S. Pat. Nos. 6,113,918; 6,303,347; 6,525,028; and 6,649,172.

Certain IRM compounds can function as Toll-like receptor (TLR) agonists, i.e., their immunomodulating influence is exerted through a TLR-mediated cellular pathway. For example, some small molecule IRMs have been identified as agonists of one or more members of the TLR receptor family, TLR2, TLR4, TLR6, TLR7, and TLR8; certain AGPs have been identified as agonists of TLR4; and, some CpGs have been identified as an agonist of TLR9. In many cases, activating a TLR-mediated pathway results in gene transcription, cytokine or co-stimulatory marker expression by activating NF-κB regardless of the particular TLR that is activated.

In certain embodiments of the present invention, the IRM is an agonist of at least one TLR. In particular embodiments, the IRM compound can be an agonist of TLR7, TLR8, and/or TLR9. In alternative embodiments, the IRM compound is an agonist of TLR4. In certain specific embodiments, the IRM is an agonist of TLR7 or an agonist of both TLR7 and TLR8. The IRM may induce the production of one or more cytokines, including but not limited to, Type I interferons, TNF-α, and IL-10. See, for example, Gibson et al., Cell Immunol. 218(1-2):74-86 (2002). The IRM may effect the maturation, activation, and/or migration of cells of the myeloid lineage, including, but not limited to, macrophages, dendritic cells, and Langerhans cells.

Suitable IRM compounds include, but are not limited to, the small molecule IRM compounds described above having a 2-aminopyridine fused to a five membered nitrogen-containing heterocyclic ring. Such compounds include, for example, imidazoquinoline amines including but not limited to amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines. Various combinations of IRMs can be used if desired.

In some embodiments, the IRM compound is an imidazoquinoline amine such as, for example, 1-(2-methylpropyl)-1H-imidazo[4,5-c]quinolin-4-amine or 4-amino-α, α-dimethyl-2-ethoxymethyl-1H-imidazo[4,5-c]quinolin-1-ethanol. In one particular embodiment, the IRM compound is 1-(2-methylpropyl)-1H-imidazo[4,5-c]quinolin-4-amine.

In an alternative embodiment, the IRM compound is an imidazonaphthyridine amine such as, for example, 2-methyl-1-(2-methylpropyl)-1H-imidazo[4,5-c][1,5]naphthyridin-4-amine or 1-(2-methylpropyl)-1H-imidazo[4,5-c][1,5]naphthyridin-4-amine.

In another alternative embodiment, the IRM compound is a sulfonamide substituted imidazoquinoline amine such as, for example, N-[4-(4-amino-2-ethyl-1H-imidazo[4,5-c]quinolin-1-yl)butyl]methanesulfonamide.

In another alternative embodiment, the IRM compound is an amide substituted imidazoquinoline amine such as, for example, N-{2-[4-amino-2-(ethoxymethyl)1H-imidazo[4,5-c]quinolin-1-yl]-1,1-dimethylethyl}cyclohexanecarboxamide.

In another alternative embodiment, the IRM compound is a thioether substituted imidazoquinoline amine such as, for example, 2-butyl-1-[2-(propylsulfonyl)ethyl]1H-imidazo[4,5-c]quinolin-4-amine.

In yet another alternative embodiment, the IRM compound is an imidazopyridine amine such as, for example, N-{2-[4-amino-2-(ethoxymethyl)-6,7-dimethyl-1H-imidazo[4,5-c]pyridin-1-yl]ethyl}benzamide.

In certain embodiments, the IRM compound may be an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

In certain embodiments, the IRM compound may be a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amine, or a 6-, 7-, 8-, or 9-aryl or heteroaryl substituted imidazoquinoline amine. As used herein, substituted imidazoquinoline amines specifically and expressly exclude 1-(2-methylpropyl)1-H-imidazo[4,5-c]quinolin-4-amine and 4-amino-α,α-dimethyl-2-ethoxymethyl-1H-imidazo[4,5-c]quinolin-1-ethanol.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

An IRM compound may be provided in any formulation suitable for administration to a subject. Suitable types of formulations are described, for example, in U.S. Pat. No. 5,736,553; 5,238,944; 5,939,090; 6,365,166; 6,245,776; 6,486,186; European Patent No. EP 0 394 026; and U.S. Patent Publication No. 2003/0199538. The compound may be provided in any suitable form including but not limited to a solution, a suspension, an emulsion, or any form of mixture. The compound may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a foam, a solution, a suspension, a dispersion, an emulsion, a microemulsion, a paste, a powder, a solid stick (e.g., wax- or petroleum-based sticks), a wipe, an oil, a lotion, and the like. In one particular embodiment, the IRM compound is provided in a cream formulation suitable for topical administration.

A formulation suitable for practicing the invention may include one or more additional active ingredients such as, for example, another IRM compound, an antibiotic, a pain reliever, a skin penetration enhancer, or a topical anesthetic. In some embodiments, the IRM compound may be incorporated into, for example, a sunscreen, a skin lotion, a skin moisturizer, or cosmetic. Alternatively, the IRM compound may be incorporated into any vehicle suitable for intradermal or transdermal delivery.

The composition of a suitable formulation may depend at least in part on many factors known in the art including, but not limited to, the physical and chemical nature of the IRM compound; the nature of the carrier; the dosing regimen; the state of the subject's immune system (e.g., suppressed, compromised, stimulated); the method of administering the IRM compound; and the desired result (e.g., accentuating margins, visualizing subclinical lesions, etc.). Accordingly it is not practical to set forth generally a single formulation suitable for diagnosing skin lesions for all possible applications. Those of ordinary skill in the art, however, can readily determine a suitable formulation with due consideration of such factors.

A suitable formulation may contain, for example, about 0.001%, about 0.002%, about 0.005%, about 0.01%, about 0.015%, about 0.02%, about 0.025%, about 0.05%, about 0.1%, about 0.25%, about 0.5%, about 0.75%, about 1%, about 2.5%, about 5%, about 7.5%, about 10%, about 25%, or about 50% active IRM compound. In one particular embodiment, the composition includes about 5% IRM compound.

The amount of IRM compound administered and the period of time over which it is administered may depend, at least in part, on the particular embodiment of the invention being practiced. In one embodiment, the IRM compound may be administered to a lesion periodically for a period of time and in an amount sufficient to permit visualization of the margins of the lesion. In some cases, administering the IRM compound may permit visualization of a subclinical lesion. In other cases, applying the IRM compound may permit more accurate visualization of the actual margin of a clinically visible lesion. The treatment may cause tissue of the lesion that had not been clinically visible to become visible, thereby increasing the likelihood that the entire lesion is visible. If occurring prior to an ablation procedure, pre-treatment with an IRM compound may increase the likelihood that the entire lesion is removed during the ablation procedure, thereby improving the likelihood of a positive treatment outcome.

Visualization of the lesion may be unaided (e.g., with the naked eye) or aided such as, for example, with a magnifying lens.

In an alternative embodiment, the IRM compound may be administered to a lesion periodically for a period of time and in an amount sufficient to visibly accentuate the margins of a skin lesion. In some cases, the margin of a lesion may appear somewhat indefinite, having margins that are, for example, diffuse or irregular. Administering an IRM compound may visibly accentuate the margin of the lesion—i.e., render the margins of the lesion more definite.

In another alternative embodiment, the IRM compound may be administered to a lesion periodically for a period of time and in an amount sufficient to "light up" the margins of a lesion by inducing a localized immune response within the lesion. The localized immune response within the lesion may be mild to moderate. The localized immune response within the lesion may be moderate to severe. The localized immune response within the lesion may result in inflammation within the lesion, which may include one or more of, for example, erosion, edema (swelling) or erythema (redness) of the lesion.

The particular amount of IRM compound necessary to permit diagnosis of a lesion in a subject may depend, at least in part, on one or more factors. Such factors include, but are not limited to, the particular IRM compound being administered; the state of the subject's overall health; the state of the subject's immune system (e.g., suppressed, compromised, stimulated); the route of administering the IRM; the particular type of lesion; the histological subtype of the lesion; the size, duration, and location of the lesion; the subject's treatment history; the presence of recurrent disease; and the desired result (e.g., margin accentuation, visualization of subclinical lesions, etc.). Accordingly, it is not practical to set forth generally the amount that constitutes an effective amount of an IRM compound. Those of ordinary skill in the art, however, can readily determine the appropriate amount with due consideration of such factors.

In some embodiments, the methods of the present invention include administering sufficient IRM compound to provide a dose of, for example, from about 100 ng/kg to about 50 mg/kg to the subject, although in some embodiments the method may be performed by administering IRM compound in a dose outside this range. In some of these embodiments, the method includes administering sufficient IRM compound to provide a dose of from about 10 µg/kg to about 5 mg/kg to the subject, for example, a dose of from about 100 µg/kg to about 1 mg/kg.

The dosing regimen may depend at least in part on many factors known in the art including but not limited to the physical and chemical nature of the IRM compound; the nature of the carrier; the amount of IRM being administered; the period over which the IRM compound is being administered; the state of the subject's immune system (e.g., suppressed, compromised, stimulated); the method of administering the IRM compound; and the desired result (e.g., accentuating margins of clinically visible lesions, visualizing subclinical lesions, etc.). Accordingly it is not practical to set forth a general dosing regimen effective for all possible applications. Those of ordinary skill in the art, however, can readily determine an appropriate dosing regimen with due consideration of such factors.

In some embodiments of the invention, the IRM compound may be administered, for example, from a single dose to multiple doses administered multiple times per day. In certain embodiments, the IRM compound may be administered from about once per week to about once per day. In one particular embodiment, the IRM compound is administered once per day, two days per week. In an alternative embodiment, the IRM compound is administered once per day, three times per week.

The period of time that is sufficient for practicing the invention may depend, at least in part, on factors such as, for example, the physical and chemical nature of the IRM compound; the nature of the carrier; the amount of IRM being administered; the frequency with which the IRM compound is being administered; the state of the subject's immune system (e.g., suppressed, compromised, stimulated); the method of administering the IRM compound; and the desired result (e.g., accentuating margins of clinically visible lesions, visualizing subclinical lesions, etc.). Accordingly it is not practical to set forth generally a sufficient period of time for all possible applications. Those of ordinary skill in the art, however, can readily determine an appropriate time period with due consideration of such factors.

In some embodiments, a sufficient period of time may range from at least one day to about six months, although in some embodiments the invention may be practiced by administering IRM compound for a period outside this range. In some embodiments, the IRM compound may be administered for at least one week. In an alternative embodiment, the IRM compound may be administered for at least about four weeks. In another alternative embodiment, the IRM compound may be administered for at least about eight weeks. In another alternative embodiment, the IRM compound may be administered for at least about sixteen weeks.

The methods of the present invention may be performed on any suitable subject. Suitable subjects include, but are not limited to, animals such as, but not limited to, humans, non-human primates, rodents, dogs, cats, horses, pigs, sheep, goats, or cows.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention. Unless otherwise indicated, all percentages and ratios are by weight.

Example 1

Pretreatment of AK Lesions with Imiquimod

Volunteers having from four to eight clinically diagnosed AK lesions located within a 25 $cm^2$ treatment area were enrolled in a study. The study consisted of a prestudy period, a 16-week treatment period, and an 8-week post treatment period. Enrolled participants were randomized to receive either 5% imiquimod cream (ALDARA, 3M Pharmaceuticals, St. Paul, Minn.) or placebo cream containing no biologically active ingredient.

Subjects were instructed to topically administer cream from a single-use sachet. Sachets that contained imiquimod contained 250 mg of cream. One group of subjects applied cream two days per week for sixteen weeks, with dosing days occurring a minimum of three days apart. A second group of subjects applied cream three days per week for sixteen weeks, with dosing days occurring at least two days apart.

At a pretreatment visit, a baseline AK lesion count was established for each subject. Updated AK lesion counts were calculated at visits after four weeks, eight weeks, and sixteen weeks of treatment. For each individual, "new" AK lesions were calculated as the difference between the updated AK count and the baseline AK count. Thus, subclinical AK lesions may become apparent after treatment with ALDARA cream. Results are shown in Table 1.

TABLE 1

| | Number (%) of Subjects with an Increase in AK Lesion Count | | | | |
|---|---|---|---|---|---|
| Treatment Group | N | Week 4 | Week 8 | Week 16 | Any |
| Imiquimod 2x/week | 215 | 79 (36.7%) | 61 (28.4%) | 20 (9.3%) | 103 (47.9%) |
| Vehicle 2x/week | 221 | 29 (13.1%) | 39 (17.6%) | 35 (15.8%) | 72 (32.6%) |
| Imiquimod 3x/week | 242 | 80 (33.1%) | 40 (16.5%) | 15 (6.2%) | 103 (42.6%) |
| Vehicle 3x/week | 250 | 26 (10.4%) | 32 (12.8%) | 25 (10.0%) | 55 (22.0%) |

Example 2

Pretreatment of BCC Lesions with Imiquimod

Prior to surgical excision of their lesions, patients with BCC lesions are pretreated with a 5% imiquimod cream, marketed as ALDARA (3M Pharmaceuticals, St. Paul, Minn.). Topical application of the 5% imiquimod cream to the BCC lesions five to seven times a week for five to seven weeks results in significant erosion, erythema, and/or edema of the BCC lesions, thereby accentuating the margins of the lesions.

Example 3

Treatment of Bowen's Lesions with Imiquimod

Prior to surgical excision of their lesions, patients with Bowen's disease are pretreated with a 5% imiquimod cream, marketed as ALDARA (3M Pharmaceuticals, St. Paul, Minn.). Topical application of the 5% imiquimod cream to the lesion two to three times a week for one to three weeks results in significant erosion, erythema, and/or edema of the lesions, thereby accentuating the margins of the lesions.

Example 4

Treatment of Lentigo Maligna Lesions with Imiquimod

Prior to surgical excision of their lesions, patients with lentigo maligna are pretreated with a 5% imiquimod cream, marketed as ALDARA (3M Pharmaceuticals, St. Paul, Minn.). Topical application of the 5% imiquimod cream to the lesion two to three times a week for one to three weeks results in significant erosion, erythema, and/or edema of the lesions, thereby accentuating the margins of the lesions.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of treating a skin lesion, the method comprising:
   administering to a treatment area that comprises at least one skin lesion having margins which are not clinically visible an immune response modifier compound, having a 2-aminopyridine fused to a five membered nitrogen-containing heterocyclic ring, for a period of time and in an amount sufficient to accentuate and permit visualization of the margins of the skin lesion; and
   subjecting the skin lesion to an ablation procedure to remove the lesion while the margins are accentuated.

2. The method of claim 1 wherein the ablation procedure is selected from the group consisting of Mohs micrographic surgery, surgical excision, cryotherapy, and radiotherapy.

3. The method of claim 1, wherein the immune response modifier compound is an imidazoquinoline amine, a tetrahydroimidazoqiuinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloqiuinoline amine, an oxazolopyridine amine, a thiazolopyridine amine, an oxazolonaphthyridine amine, or a thiazolonaphthyridine amine.

* * * * *

UNITED STATES PATENT AND TRADEMARK OFFICE
CERTIFICATE OF CORRECTION

PATENT NO. : 7,699,057 B2
APPLICATION NO. : 10/799997
DATED : April 20, 2010
INVENTOR(S) : Richard L. Miller et al.

It is certified that error appears in the above-identified patent and that said Letters Patent is hereby corrected as shown below:

On the Title Page, Item (56), Under "Other Publications"
Line 4, delete "Study," and insert -- Society, --, therefor.
Line 18, delete "Gessellschaft" and insert -- Gesellschaft --, therefor.
Line 18, delete "lmmunologie," and insert -- Immunologie, --, therefor.

Column 7
Line 27, before "(such" delete "derivatives".

Column 8
Lines 45-46, delete "4-amino-α, α-dimethyl" and insert -- 4-amino-α,α-dimethyl --, therefor.
Line 61, delete "(ethoxymethyl)1H" and insert -- (ethoxymethyl)-1H --, therefor.
Line 66, delete "ethyl]1H" and insert -- ethyl]-1H --, therefor.

Column 9
Line 31, delete "1-(2-methylpropyl)1-H" and insert -- 1-(2-methylpropyl)-1H --, therefor.
Line 43, delete "No." and insert -- Nos. --, therefor.

Column 14
Lines 28-29, Claim 3, delete "tetrahydroimidazoqiuinoline" and insert
-- tetrahydroimidazoquinoline --, therefor.
Line 33, Claim 3, delete "thiazoloqiuinoline" and insert -- thiazoloquinoline --, therefor.

Signed and Sealed this
Thirty-first Day of May, 2011

David J. Kappos
*Director of the United States Patent and Trademark Office*